United States Patent [19]

Kondo

[11]  4,336,410

[45]  Jun. 22, 1982

[54] PROCESS FOR ABSORPTIVE SEPARATION OF CYCLOHEXENE

[75] Inventor: Tsuneyuki Kondo, Nagoya, Japan

[73] Assignee: Toray Industries, Inc., Tokyo, Japan

[21] Appl. No.: 250,548

[22] Filed: Apr. 3, 1981

[30] Foreign Application Priority Data

Apr. 7, 1980 [JP] Japan ................................ 55/44573

[51] Int. Cl.³ ..................... C07C 7/12; C10G 25/00; C10G 25/02
[52] U.S. Cl. ....................................... 585/827; 585/831
[58] Field of Search ............................ 585/827, 831; 208/310 Z

[56] References Cited

U.S. PATENT DOCUMENTS

| | | | |
|---|---|---|---|
| 3,078,643 | 2/1963 | Milton | 585/827 |
| 3,600,453 | 8/1971 | Reichenbacher et al. | 208/310 Z |
| 3,700,744 | 10/1972 | Berger et al. | 585/831 |
| 3,723,302 | 3/1973 | Pharis et al. | 208/310 Z |
| 3,761,533 | 9/1973 | Otani et al. | 585/827 |
| 3,851,006 | 11/1974 | De Rosset et al. | 585/827 |
| 3,979,280 | 9/1976 | Dielacher et al. | 585/827 |

FOREIGN PATENT DOCUMENTS

| | | | |
|---|---|---|---|
| 49-116032 | 6/1974 | Japan | 585/831 |
| 55-98122 | 7/1980 | Japan | 585/827 |

*Primary Examiner*—Delbert E. Gantz
*Assistant Examiner*—Helane E. Maull
*Attorney, Agent, or Firm*—Austin R. Miller

[57] ABSTRACT

Cyclohexene can be advantageously separated from a mixture containing as main components benzene, cyclohexene and cyclohexane by a process wherein said mixture is brought into contact with a type X aluminosilicate zeolite, which has been ion-exchanged with a silver ion, as an adsorbent, whereby cyclohexene is selectively adsorbed thereon, and then, cyclohexene is desorbed therefrom. The desorption of cyclohexene is preferably carried out by using a desorbent, such as an alkylbenzene having 7 or 8 carbon atoms in the molecule.

8 Claims, No Drawings

PROCESS FOR ABSORPTIVE SEPARATION OF CYCLOHEXENE

BACKGROUND OF THE INVENTION

1. Field of the Invention

This invention relates to a process for the adsorptive separation of cyclohexene from a mixture containing as main components benzene, cyclohexene and cyclohexane.

2. Description of the Prior Art

A mixture containing as main components benzene, cyclohexene and cyclohexane is ordinarily obtained as a reaction product in the process for preparing cyclohexene, for example, by selective hydrogenation of benzene, selective dehydrogenation of cyclohexane or oxidative dehydrogenation of cyclohexane.

Cyclohexene is a starting material for use in the synthsis of organic compounds such as cyclohexanol and adipic acid. In order to obtain cyclohexene from the above-mentioned mixture advantageously on an industrial scale, the separating and purifying operation of the reaction mixture is very important. There have been proposed various processes for separating cyclohexene from the above-mentioned reaction mixture.

For example, there has been proposed a method comprising passing the reaction mixture through a specially treated cation exchange resin to separate the mixture into the respective components. According to this process, the intended separation can be attained by simple procedures. This process, however, is still not satisfactory in that dissolution of the ion exchange resin into the mixture takes place, deterioration of the ion exchange resin occurs, the purity of the separated product is low and a purification step becomes necessary for enhancing the purity, with the result that the process becomes complicated.

We made researches with a view to overcoming these defects of the above-mentioned conventional process, and we found that when cyclohexene is separated and recovered from a mixture containing benzene and/or cyclohexane and cyclohexene, if a type X aluminosilicate zeolite capable of selectively adsorbing benzene and/or cyclohexene is used as an adsorbent, cyclohexene of a high purity can be separated simply and relatively advantageously. We have already proposed this process (see Japanese Laid-open Patent Application No. 41,844/79).

When cyclohexene is separated from a ternary mixture containing benzene, cyclohexene and cyclohexane according to the above-mentioned process, this separation must be carried out by the following two sequential separating steps: (1) the step of removing benzene from the mixture by selective adsorption and (2) the step of separating cyclohexene from the remaining binary mixture comprising cyclohexene and cyclohexane by selective adsorption. This is because these three components tend to be adsorbed on the above adsorbent in the order of benzene, cyclohexene and then, cyclohexane.

SUMMARY OF THE INVENTION

It has now been found surprisingly that if a type X aluminosilicate zeolite which has been ion-exchanged with a silver ion is used as an adsorbent for a ternary mixture comprising benzene, cyclohexene and cyclohexane, cyclohexene is first selectively adsorbed and therefore, it becomes possible to adsorptively separate cyclohexene by a single separating step without the preliminary adsorptive removal of benzene, and further that if an alkyl benzene having 7 or 8 carbon atoms in the molecule is used as a desorbent, the cyclohexene adsorbed on the specified aluminosilicate zeolite can be advantageously desorbed therefrom.

In accordance with the present invention, there is provided an improved process for separting cyclohexene from a mixture containing as main components benzene, cyclohexene and cylohexane wherein said mixture is brought into contact with a type X aluminosilicate zeolite as an adsorbent which has been ion-exchanged with a silver ion, whereby cyclohexene is selectively adsorbed therein. The cyclohexene adsorbed on the specified aluminosilicate zeolite is advantageously desorbed therefrom by using as a desorbent an alkylbenzene having 7 or 8 carbon atoms in the molecule.

DESCRIPTION OF THE PREFERRED EMBODIMENTS

As the mixture containing as main components benzene, cyclohexene and cyclohexane, there are ordinarily used, for example, reaction product mixtures obtained by selective hydrogenation of benzene, selective dehydrogenation of cyclohexane or oxidative dehydrogenation of cyclohexane. Accordingly, the composition of the respective components in the mixture is not particularly limited but optional. Moreover, the mixture may further comprise small quantities of reaction byproducts, for example, unsaturated hydrocarbons such as 1,3-cyclohexadiene, 1,4-cyclohexadiene and methylcyclopentene and other hydrocarbons, though the kinds of included byproducts differ depending upon the reaction adopted for the preparation of cyclohexene.

In the case where the above-mentioned reaction product contains water and is separated into two phases, it is preferred that the reaction product be used after the aqueous layer has been separated therefrom. In this case, better results are obtained if water dissolved in the reaction mixture is removed in advance by appropriate means.

For example, the reaction product can be separated from water by distillation. Furthermore, water alone can be adsorptively removed by using a zeolite incapable of substantially adsorbing any of the benzene, cyclohexene and cyclohexane (for example, a type A synthetic aluminosilicate zeolite manufactured and supplied by Union Carbide Corporation, U.S.A.).

By the term "type X aluminosilicate zeolite" used herein is meant a zeolite having a crystal structure similar to that of faujasite and has a composition represented by the following formula:

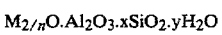

$$M_{2/n}O \cdot Al_2O_3 \cdot xSiO_2 \cdot yH_2O$$

wherein M stands for a metal, n stands for the valency of the metal M, x is a number of from 2 to 3, and y designates the content of water crystallization. Any of type X aluminosilicate zeolites having the above-mentioned crystal structure and composition can be used in the present invention. Furthermore, the preparation process is not particularly critical, and any of the type X aluminosilicate zeolites synthetized by known processes can be used in the present invention.

The metal M in the type X aluminosilicate zeolite that is used in the present invention is not critical but optional, but it is indispensable that a part of the metal be ion-exchanged with a silver ion (Ag+). In other words, the metal ions constituting the zeolite that is used in the present invention comprise ions of silver and at least one other metal. Known ion exchange techniques may be adopted. For example, in the case where the ion exchange is effected by using silver nitrate, the intended ion exchange can be attained by contacting the type X aluminosilicate zeolite with an aqueous silver nitrate solution having a concentration of 0.1 to 10% by weight. This contact can be conducted batchwise or according to a circulation method. The applicable temperature may be in the range of from 0° C. to 100° C. It is preferred that the degree of ion exchange with silver ions be such that the silver ions occupy at least 20 mole %, especially 20 to 90 mole %, of the total metal ions. The degree of ion exchange can optionally be adjusted by appropriately controlling the ion exchange temperature, the solution concentration, the frequency of treatment and the manner of treatment. After completion of the ion exchange treatment, the zeolite is sufficiently washed with water until nitric ions ($NO_3^-$) or silver ions are not detected.

It is indispensable that water of crystallization be removed in advance before the silver ion-exchanged type X aluminosilicate zeolite is used as the adsorbent. Ordinarily, the zeolite is heated at a temperature of at least 100° C. to reduce the content of water of crystallization. It is preferred that the zeolite be heated at 200° to 700° C. to substantially remove water of crystallization. If the heating is carried out at a temperature lower than 100° C., only a minor part of water can be removed, and therefore, the adsorption amount of benzene and the like is decreased. If the heating is carried out at a temperature exceeding 700° C., the crystal structure of the silver ion-exchanged type X aluminosilicate zeolite is often destroyed, resulting in reduction of the adsorbability.

The silver ion-exchanged type X aluminosilicate zeolite may be in a powder form or a granulated lump form, or it may be in the form of a shaped body obtained using, for example, an extruder, a granulator or a pelletizer. A binder is ordinarily used for molding, but if a satisfactory shaped body can be obtained without use of a binder, a binder need not be used at all. As the binder, there can be used, for example, alumina, silica, kaolin and acid clay.

Cyclohexene can be separated and recovered by subjecting the zeolite which has selectively adsorbed cyclohexene thereon to a known customary desorption treatment.

As the desorption treatment, there can be adopted, for example, a method in which the zeolite is brought into contact with a desorbent, a method in which an inert gas is circulated through the zeolite-packed column under heating and a method in which the zeolite is heated under reduced pressure. Among these methods, the method using a desorbent is preferred.

Any of the desorbents can be used in the present invention, if the following conditions are satisfied: (1) the desorbent is capable of expelling cyclohexene selectively adsorbed on the silver ion-exchanged type X aluminosilicate zeolite by the desorption operation; (2) the desorbent which is adsorbed on the zeolite adsorbent upon expelling the adsorbed cyclohexene therefrom can be expelled from the zeolite adsorbent by the desorption operation and can be used repeatedly; and (3) the desorbent can easily be separated from cyclohexene or a mixture of cyclohexane and benzene.

In the present invention, any of the desorbents can be used if the foregoing conditions are satisfied, but in the present invention, an alkylbenzene having 7 or 8 carbon atoms in the molecule is especially preferred as the desorbent. As such alkylbenzene, there can be used toluene, ethylbenzene, o-xylene, m-xylene and p-xylene.

The desorbent may be used singly or in combination with another desorbent. Furthermore, the desorbent of the present invention may be used in the form of a mixture with another compound. The kind of the compound used in such a mixture with the desorbent of the present invention is not particularly limited. For example, the desorbent of the present invention may be used in a state diluted with a paraffin or cycloparaffin.

The adsorption and desorption procedures may be carried out at a temperature of from 0° C. to 300° C., preferably from room temperature to 200° C., and at a pressure of from atmospheric pressure to 40 kg/cm$^2$, preferably from substantially atmospheric pressure to 30 kg/cm$^2$.

The adsorption and desorption procedures may be carried out either in the liquid phase or in the gas phase, but the liquid phase is ordinarily preferred.

The mixture of cyclohexane and benzene which is left after the desorption and separation of cyclohexene in the present invention can be subjected to the adsorptive separation of benzene using a zeolite type adsorbent, a silica type adsorbent or a carbonaceous adsorbent. Furthermore, known separation methods, for example, an extraction method using a specific extractant, an extraction distillation method, a separation method using an ion exchange resin and a fractional distillation method, can also be adopted.

Moreover, there may be adopted a method in which the mixture of cyclohexane and benzene is not separated into the respective components but is subjected to hydrogenation to convert all or the majority of benzene present in the mixture to cyclohexane. Moreover, the mixture may be utilized after all or the majority of the cyclohexane present in the mixture has been converted to benzene by dehydrogenation.

The adsorptive separation of cyclohexene from a mixture comprising as main components benzene, cyclohexene and cyclohexane according to the present invention includes as the basic operation steps the adsorption step of selectively adsorbing cyclohexene from the above mixture and the desorption step of expelling and recovering, by a desorbent, the cyclohexene selectively adsorbed on the adsorbent. It is preferred that these two operations be conducted in a continuous manner. More specifically, in the adsorption operation, by bringing the above mixture into contact with an adsorbent which has preliminarily adsorbed a desorbent, cyclohexene is adsorbed on the adsorbent while the desorbent is expelled from the adsorbent by cyclohexene. Accordingly, the raffinate consists mainly of the desorbent, benzene and cyclohexane, and the mixture of benzene and cyclohexane is separated and recovered from the desorbent by distillation utilizing the boiling point difference. In the subsequent desorption operation, by contacting the adsorbent, which has adsorbed cyclohexene thereon by the adsorption operation, with the desorbent, the desorbent is adsorbed on the adsorbent while cyclohexene is expelled by the desorbent. Accordingly, the extract consists mainly of cyclohexene and the desorbent. Both the components are separated and recovered by distillation utilizing the boiling point difference. The cyclohexene recovered is utilized as a product and the desorbent is recycled to be used again.

The present invention will now be described in detail with reference to the following Examples that by no means limit the scope of the invention.

The capacities of the adsorbent and desorbent used in the Examples are expressed by the selective adsorption coefficients defined by the following formulae:

$$\alpha_{HX/BZ} = \frac{(HX \text{ adsorbed on adsorbent})/(BZ \text{ adsorbed on adsorbent})}{(HX \text{ of liquid phase in equilibrium with adsorbed phase})/(BZ \text{ of liquid phase in equilibrium with adsorbed phase})}$$

$$\alpha_{HX/A} = \frac{(HX \text{ adsorbed on adsorbent})/(A \text{ adsorbed on adsorbent})}{(HX \text{ of liquid phase in equilibrium with adsorbed phase})/(A \text{ of liquid phase in equilibrium with adsorbed phase})}$$

In the above formulae, BZ stands for benzene, HX stands for cyclohexene and A stands for a desorbent.

It is preferred that the selective adsorption coefficient $\alpha_{HX/BZ}$ of cyclohexene and benzene be as high as possible. If the coefficient $\alpha_{HX/BZ}$ is low, a large quantity of the adsorbent is necessary for the adsoptive separation of cyclohexene and the recovery ratio of cyclohexene per unit amount of the adsorbent is reduced, resulting in an increase of the energy cost and also in economical disadvantages.

Furthermore, it is preferred that the selective adsorption coefficient $\alpha_{HX/A}$ of cyclohexene and the desorbent be close to 1. If the coefficient $\alpha_{HX/A}$ is too large, when cyclohexene adsorbed on the adsorbent is desorbed by the desorbent A, a large quantity of the desorbent must be used. In contrast, if the coefficient $\alpha_{HX/A}$ is too small, when cyclohexene is desorbed by contacting the adsorbent having the desorbent A adsorbed thereon with a solution of the above-mentioned mixture, cyclohexene is not sufficiently adsorbed and the efficiency of separation of cyclohexene from benzene is reduced. In general, the value $\alpha_{HX/A}$ differs depending on the adsorption conditions such as the adsorption temperature and the composition of the above mixture. If the value $\alpha_{HX/BZ}$ is sufficiently large, the range of applicable values of $\alpha_{HX/A}$ will be expanded. Accordingly, the range of applicable values of $\alpha_{HX/A}$ is influenced by the value of $\alpha_{HX/BZ}$. Therefore, it is difficult to practically define the range of values of $\alpha_{HX/A}$, but is is preferred that the value $\alpha_{HX/A}$ be in the range of from 0.1 to 5, especially from 0.2 to 4 and particularly especially from 0.7 to 3.

EXAMPLES 1 THROUGH 5

Zeolite particles having a particle size of 24 to 16 mesh (dried at 500° C. for 1 hour) were prepared by granulating a type X synthetic aluminosilicate zeolite powder (Molecular Sieve 13X manufactured and supplied by Union Carbide Corporation) by using an alumina sol. 50 g of the zeolite particles were contacted with 500 ml of a 2.55% by weight aqueous solution of silver nitrate at 5° C. for 1 hour to effect an ion exchange. Then, the zeolite was sufficiently washed with water. The amount of the exchanged silver ion was 30.5 mole %.

The zeolite was calcined in air at 500° C. for 1 hour and was naturally cooled in a phosphorus pentoxide desiccator, and about 1.7 g of the dried zeolite was used as the adsorbent.

Then, about 2 g of a mixture comprising cyclohexane (CX), cyclohexene (HX), benzene (BZ) and a desorbent (A) shown in Table 1, below, at a CX/HX/BZ/A weight ratio of 0.176/0.163/0.172/0.489 was contacted with the above-mentioned adsorbent at 80° C. for 1 hour in a completely sealed autoclave.

From the change of the composition of the mixture, the selective adsorption coefficients $\alpha_{HZ/BZ}$ and $\alpha_{HX/A}$ were determined to obtain the results shown in Table 1, below.

TABLE 1

| Example No. | Desorbent (A) | $\alpha_{HX/BZ}$ | $\alpha_{HX/A}$ |
|---|---|---|---|
| 1 | Toluene | 1.9 | 1.6 |
| 2 | Ethylbenzene | 1.5 | 1.8 |
| 3 | o-Xylene | 2.5 | 1.6 |
| 4 | m-Xylene | 1.8 | 2.3 |
| 5 | p-Xylene | 1.8 | 2.3 |

From the results shown above, it is seen that in each of the above desorbents, the value $\alpha_{HX/BZ}$ is larger than 1 and cyclohexene is adsorbed more selectively than benzene. Furthermore, the value $\alpha_{HX/A}$ is as small as 1.6 to 2.3 and each desorbent can practically be used. Among the foregoing desorbents, o-xylene is most preferred because the value $\alpha_{HX/BZ}$ of o-xylene is the highest and the value $\alpha_{HX/A}$ of o-xylene is the closest to 1.

EXAMPLES 6 AND 7

The procedures of Example 1 were repeated in the same manner except that the temperature for contact of the zeolite particles with the mixture (i.e., the adsorption temperature) was changed to 100° C. or 200° C. The results are shown in Table 2, below:

TABLE 2

| Example No. | Adsorption temperature (°C.) | $\alpha_{HX/BZ}$ | $\alpha_{HX/A}$ |
|---|---|---|---|
| 6 | 100 | 1.6 | 1.4 |
| 7 | 120 | 1.4 | 1.3 |

Both the values $\alpha_{HX/BZ}$ and $\alpha_{HX/A}$ were small, but the adsorptive separation was practically possible.

EXAMPLES 8 THROUGH 11

The procedures of Example 3 were repeated in the same manner except that the adsorption temperature was changed to 100° C., 120° C., 130° C. or 140° C. The results are shown in Table 3, below.

TABLE 3

| Example No. | Adsorption temperature (°C.) | $\alpha_{HX/BZ}$ | $\alpha_{HX/A}$ |
|---|---|---|---|
| 8 | 100 | 2.1 | 1.7 |
| 9 | 120 | 1.7 | 1.5 |
| 10 | 130 | 1.4 | 1.1 |
| 11 | 140 | 1.2 | 0.98 |

As the adsorption temperature is elevated, both the values $\alpha_{HX/BZ}$ and $\alpha_{HX/A}$ are reduced, but at 140° C., both the values are close to 1 and the selectivity of the adsorption is reduced.

EXAMPLES 12 THROUGH 14

The procedures of Example 6 were repeated in the same manner except that the composition was changed as indicated in Table 4, below. The results are shown in Table 4, below.

TABLE 4

| Example No. | Composition of mixture (CX/HZ/BZ/A) (wt. ratio) | $\alpha_{HX/BZ}$ | $\alpha_{HX/A}$ |
|---|---|---|---|
| 12 | 0.04/0.03/0.04/0.89 | 3.0 | 6.9 |
| 13 | 0.09/0.08/0.09/0.74 | 2.7 | 3.9 |
| 14 | 0.27/0.26/0.27/0.20 | 1.3 | 0.6 |

Both the values $\alpha_{HX/BZ}$ and $\alpha_{HX/Z}$ are changed according to the concentration of o-xylene (A). In Example 12, though the value $\alpha_{HX/A}$ is as large as 6.0, since the value $\alpha_{HX/BZ}$ is as large as 3.0, HX can sufficiently be separated from BZ.

EXAMPLES 15 THROUGH 19 AND COMPARATIVE EXAMPLES 1 THROUGH 3

The procedures of Example 3 were repeated in the same manner except that the ion exchange treatment using silver ions was changed and the resulting zeolite having an ion exchange ratio shown in Table 5, below was used as the adsorbent. The results are shown in Table 5, below.

TABLE 5

| | Silver ion exchange ratio (mole %) | $\alpha_{HX/BZ}$ | $\alpha_{HX/A}$ |
|---|---|---|---|
| Example 14 | 28.1 | 2.5 | 1.8 |
| Example 15 | 34.2 | 2.3 | 1.8 |
| Example 16 | 37.5 | 2.7 | 2.1 |
| Example 17 | 58.9 | 2.1 | 2.0 |
| Example 18 | 93.7 | 1.4 | 2.9 |
| Example 19 | 99.0 | 1.4 | 2.6 |
| Comparative Example 1 | 0 | 0.1 | 0.2 |
| Comparative Example 2 | 6.8 | 0.3 | 0.4 |
| Comparative Example 3 | 19.0 | 1.0 | 1.0 |

If the silver ion exchange ratio is higher than 20 mole %, the value $\alpha_{HX/BZ}$ is larger than 1 and cyclohexene can selectively be adsorbed. At a silver ion exchange ratio higher than about 90 mole %, the value $\alpha_{HX/BZ}$ is decreased to 1.4, but cyclohexene is substantially adsorbed. Since the value $\alpha_{HX/A}$ tends to increase with an increase of the silver ion exchange ratio, it is preferred that the silver ion exchange ratio be in the range of about 20 mole % to about 90 mole %.

EXAMPLES 20 THROUGH 25 AND COMPARATIVE EXAMPLES 4 AND 5

The procedures of Example 1 were repeated in the same manner except that the calcination temperature of the adsorbent was changed as shown in Table 6, below. The results are shown in Table 6, below.

TABLE 6

| | Calcination temperature of adsorbent (°C.) | $\alpha_{HX/BZ}$ | $\alpha_{HX/A}$ |
|---|---|---|---|
| Example 20 | 200 | 1.8 | 2.1 |
| Example 21 | 300 | 2.0 | 1.6 |
| Example 22 | 400 | 1.9 | 1.5 |
| Example 23 | 500 | 1.9 | 1.6 |
| Example 24 | 600 | 1.8 | 1.6 |
| Example 25 | 700 | 1.7 | 1.5 |
| Comparative Example 4 | 100 | 2.4 | 4.6 |
| Comparative Example 5 | 800 | Measurement impossible | Measurement impossible |

As is seen from the results shown in Table 6, when the calcination temperature of the adsorbent is in the range of from 200° C. to 700° C., both the values $\alpha_{HX/BZ}$ and $\alpha_{HX/A}$ tend to decrease to some extent as the calcination temperature is elevated. However, it may be said that there is no substantial difference if the calcination temperature is in the above-mentioned range.

When the calcination was carried out at 100° C. in Comparative Example 4, the adsorption capacity was several % and it was found that the adsorbent cannot practically be used. When the calcination was carried out at 800° C., the adsorption capacity was substantially zero and, therefore, measurement was impossible. The reason is that, since the calcination temperature was too high, the crystal structure of the zeolite was destroyed.

COMPARATIVE EXAMPLES 6 THROUGH 8

The procedure of Example 3 were repeated in the same manner except that a zeolite shown in Table 7, below was used as the adsorbent. The results are shown in Table 7, below.

TABLE 7

| Comparative Example No. | Adsorbent | $\alpha_{HX/BZ}$ | $\alpha_{HX/A}$ |
|---|---|---|---|
| 6 | NaY (type Y synthetic zeolite manufactured and supplied by Union Carbide Corporation, U.S.A.) | 0.1 | 0.1 |
| 7 | AgY (zeolite obtained by ion-exchanging zeolite of Comparative Example 6 with 45.6 mole % of Ag) | 0.8 | 2.1 |
| 8 | AgY (zeolite obtained by ion-exchanging zeolite of Comparative Example 6 with 64.6 mole % of Ag) | 0.8 | 2.6 |

From the results shown in Table 7, it is seen that when a type Y aluminosilicate zeolite is used, even if the zeolite is ion-exchanged with silver ions, the value $\alpha_{HX/BZ}$ is smaller than 1 and cyclohexene is not adsorbed more selectively than benzene.

I claim:

1. An improvement in a process for separating cyclohexene from a mixture containing as main components benzene, cyclohexene and cyclohexane wherein said mixture is brought into contact with a type X aluminosilicate zeolite as an adsorbent whereby cyclohexene is selectively adsorbed thereon, and then, cyclohexene is desorbed therefrom, said improvement comprising using as an adsorbent a type X aluminosilicate zeolite which has been ion-exchanged with a silver ion.

2. The process according to claim 1 wherein the degree of ion exchange with silver ions is such that the silver ions occupy at least 20 mole % of the total metal ions present in the silver ion-exchanged type X aluminosilicate zeolite.

3. The process according to claim 1 wherein the degree of ion exchange with silver ions is such that the silver ions occupy 20 to 90 mole % of the total metal ions present in the silver ion-exchanged type X aluminosilicate zeolite.

4. The process according to claim 1 wherein the silver ion-exchanged type X aluminosilicate zeolite is subjected to dehydration whereby the water of crystallization is substantially removed therefrom prior to the cyclohexene-containing mixture being brought into contact therewith.

5. The process according to claim 1 wherein cyclohexene selectively adsorbed on the silver ion-exchanged type X aluminosilicate zeolite is desorbed therefrom by using a desorbent.

6. The process according to claim 5 wherein the desorbent is an alkylbenzene having 7 or 8 carbon atoms in the molecule.

7. The process according to claim 5 or 6 wherein the adsorption and desorption are carried out at a temperature of 0° to 300° C. and at a pressure of from atmospheric pressure to 40 kg/cm$^2$.

8. The process according to any one of claims 1 to 6 wherein the selective adsorption of cyclohexene and the desorption thereof are carried out in a continuous manner.

* * * * *